United States Patent
Guillon et al.

(10) Patent No.: US 10,919,029 B2
(45) Date of Patent: Feb. 16, 2021

(54) MODIFIED CATALYST WITH STRUCTURE TYPE MTW, A METHOD FOR ITS PREPARATION AND ITS USE IN A PROCESS FOR THE ISOMERIZATION OF AN AROMATIC C8 CUT

(71) Applicant: IFP Energies Nouvelles, Rueil-Malmaison (FR)

(72) Inventors: Emmanuelle Guillon, Vourles (FR); Laure Brandhorst, Lyons (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 444 days.

(21) Appl. No.: 15/829,316

(22) Filed: Dec. 1, 2017

(65) Prior Publication Data
US 2018/0085742 A1    Mar. 29, 2018

Related U.S. Application Data

(62) Division of application No. 14/654,117, filed as application No. PCT/FR2013/052942 on Dec. 4, 2013, now abandoned.

(30) Foreign Application Priority Data

Dec. 20, 2012    (FR) .................... 12 03535

(51) Int. Cl.
| | | |
|---|---|---|
| *B01J 29/74* | (2006.01) | |
| *B01J 37/08* | (2006.01) | |
| *B01J 37/18* | (2006.01) | |
| *B01J 37/10* | (2006.01) | |
| *B01J 29/72* | (2006.01) | |
| *B01J 29/76* | (2006.01) | |
| *B01J 35/10* | (2006.01) | |
| *B01J 37/00* | (2006.01) | |
| *B01J 37/02* | (2006.01) | |
| *C07C 5/27* | (2006.01) | |

(52) U.S. Cl.
CPC .......... *B01J 29/74* (2013.01); *B01J 29/7269* (2013.01); *B01J 29/7469* (2013.01); *B01J 29/7669* (2013.01); *B01J 35/108* (2013.01); *B01J 35/1042* (2013.01); *B01J 35/1047* (2013.01); *B01J 37/0009* (2013.01); *B01J 37/0201* (2013.01); *B01J 37/08* (2013.01); *B01J 37/10* (2013.01); *B01J 37/18* (2013.01); *C07C 5/2737* (2013.01); *C07C 5/2775* (2013.01); *B01J 2229/14* (2013.01); *B01J 2229/18* (2013.01); *B01J 2229/36* (2013.01); *B01J 2229/42* (2013.01); *C07C 2529/74* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 4,784,747 A * | 11/1988 | Shihabi | B01J 29/40 208/111.15 |
| 5,763,720 A | 6/1998 | Buchanan et al. | |
| 7,939,701 B2 | 5/2011 | Whitchurch et al. | |
| 2004/0087823 A1* | 5/2004 | McMinn | C07C 5/2737 585/481 |
| 2009/0093662 A1 | 4/2009 | Whitchurch et al. | |
| 2011/0077146 A1 | 3/2011 | Whitchurch et al. | |
| 2013/0041194 A1 | 2/2013 | Ballegoy et al. | |
| 2014/0179969 A1 | 6/2014 | Nenu et al. | |

FOREIGN PATENT DOCUMENTS

| | | |
|---|---|---|
| EP | 2047906 A1 | 4/2009 |
| WO | 2009076024 A1 | 6/2009 |
| WO | 2010000652 A1 | 1/2010 |
| WO | 2012066012 A1 | 5/2012 |

OTHER PUBLICATIONS

International Search Report dated Mar. 6, 2014 issued in corresponding PCT/FR2013/052942 application (pp. 1-6).

* cited by examiner

*Primary Examiner* — Colin W. Slifka
(74) *Attorney, Agent, or Firm* — Millen White ZeLano and Branigan, PC; John Sopp

(57) ABSTRACT

The invention concerns a catalyst comprising at least one zeolite with structure type MTW, a matrix, at least one metal from group VIII of the periodic classification of the elements, said catalyst having a mesopore volume increased by at least 10% compared with its initial mesopore volume, which is generally in the range 0.55 to 0.75 mL/g, at the end of a treatment with steam at a partial pressure in the range 0.01 to 0.07 MPa and at a temperature in the range 300° C. to 400° C. for at least 0.5 hour. The invention concerns the process for the preparation of said catalyst as well as an isomerization process employing said catalyst.

20 Claims, No Drawings

MODIFIED CATALYST WITH STRUCTURE TYPE MTW, A METHOD FOR ITS PREPARATION AND ITS USE IN A PROCESS FOR THE ISOMERIZATION OF AN AROMATIC C8 CUT

FIELD OF THE INVENTION

The present invention relates to a catalyst comprising a zeolite with structure type MTW, modified by a treatment with steam.

The invention also relates to the preparation of the catalyst of the invention and to the use of said catalyst in a process for the isomerization of aromatic compounds containing 8 carbon atoms per molecule.

The isomerization process is of particular application to the isomerization of aromatic compounds containing 8 carbon atoms per molecule into para-xylene, and more particularly to the isomerization of ethylbenzene into para-xylene.

PRIOR ART

Isomerization of the aromatic C8 cut (aromatic compounds containing 8 carbon atoms per molecule) is the principal pathway to the formation of para-xylene, a product which is highly sought-after in the petrochemicals industry; it is primarily used for the manufacture of polyester fibres and films. The aromatic C8 cut obtained from catalytic reforming or steam cracking comprises meta-, para- and ortho-xylene as well as ethylbenzene. The cost of separating out the ethylbenzene by distillation is too high, and so only the para-xylene and possibly ortho-xylene are separated by selective separation over zeolites using various separation processes. The residual C8 cut comprising ethylbenzene is then transformed in an isomerization unit, the aim being to maximize the para-xylene fraction and to transform the ethylbenzene into xylenes or into benzene.

Xylene isomerization occurs in accordance with a monofunctional acid mechanism, the acid function generally being supplied by a zeolite. In contrast, ethylbenzene transformation requires a bifunctional catalyst having both an acid function and a hydrogenating function. In existing processes, the ethylbenzene is either isomerized into xylenes or dealkylated to form benzene. Thus, the isomerization is said to be either isomerizing or dealkylating.

The catalysts employed are generally bifunctional catalysts bringing together a zeolitic phase, at least one metal and a binder (also termed the matrix).

ZSM-12, a zeolite with structure type MTW, is one of the zeolites used for the isomerization of C8 aromatic cuts. These catalysts have been described in particular in patent applications WO 2010/000652 A1 and WO 2012/066012 A1.

An improvement to zeolitic catalysts for isomerizing isomerization to form xylenes would consist in increasing the ethylbenzene conversion; this step is the most difficult in this transformation. In particular, secondary side reactions such as dismutation and dealkylation of ethylbenzene limit upgrading of this compound into xylenes.

One pathway to improvement consists of modifying the catalyst using various treatments which can cause changes in the characteristics of the zeolite and/or the binder used. One particular treatment is steam treatment (also known as steaming).

U.S. Pat. No. 4,784,747 describes catalysts which have undergone steam treatment, which means that the catalytic activity can be increased, in particular for cracking and dewaxing. The best performances were obtained for steam treatment between 200° C. and 500° C.

Patent EP 034 444 B2 describes catalysts, in particular ZSM-5, which have undergone a steam treatment at a partial pressure of water of less than 100 mbar (1 bar=0.1 MPa) in order to increase their activity for n-hexane cracking.

The Applicant has discovered that a zeolitic catalyst comprising at least one MTW type zeolite which has undergone a particular treatment in the presence of steam exhibits a substantial improvement in ethylbenzene conversion and approach to thermodynamic equilibrium for para-xylene during its use in a process for the isomerizing isomerization of an aromatic C8 cut comprising at least ethylbenzene.

DETAILED DESCRIPTION OF THE INVENTION

The Catalyst

The present invention concerns a catalyst comprising at least one zeolite with structure type MTW, a matrix, at least one metal from group VIII of the periodic classification of the elements (corresponding to groups 8 to 10 of the new periodic classification of the elements, CRC Handbook of Chemistry and Physics, 2000-2001), said catalyst having a mesopore volume increased by at least 10%, preferably by at least 10.5% compared with its initial mesopore volume (generally in the range 0.55 to 0.75 mL/g) at the end of a treatment with steam at a partial pressure in the range 0.01 to 0.07 MPa and at a temperature in the range 300° C. to 400° C. for at least 0.5 hour.

The mesopore volume of a catalyst is obtained by subtracting the micropore volume from the pore volume of the catalyst. The micropore volume and the pore volume are deter mined from the nitrogen adsorption isotherm respectively by the t method and by the adsorbed nitrogen method (mL/g) at a relative pressure of 0.95, in accordance with the book Adsorption by Powders, F. Rouquerol et al., Academic Press 1999.

It has been observed that treatment of a catalyst with steam under particular controlled conditions, i.e. at a partial pressure in the range 0.01 to 0.07 MPa and at a temperature in the range 300° C. to 400° C., for at least 0.5 hour, can be used to increase the conversion to ethylbenzene and the approach to thermodynamic equilibrium for para-xylene during use of the treated catalyst in a process for the isomerizing isomerization of an aromatic C8 cut containing at least ethylbenzene.

Without wishing to be bound by any particular theory, this increase in the conversion could be said to be linked in part to the increase in the mesopore volume of the catalyst resulting from the steam treatment as described above.

Advantageously, the steam treatment is carried out with a partial pressure of steam in the range 0.04 to 0.06 MPa, preferably diluted in air.

Advantageously, the steam treatment is carried out at a temperature in the range 300° C. to 380° C. for 0.5 hour to 24 hours, preferably 1 hour to 12 hours.

The zeolite with structure type MTW used is preferably a zeolite selected from the group formed by the zeolites ZSM-12, CZH-5, NU-13, TPZ-12, Theta-3 and VS-12; preferably, the zeolite is ZSM-12 zeolite.

ZSM-12 zeolite is a well-known zeolite with a structure based on aluminosilicate and which might include one or more other elements. Many methods for obtaining this zeolite are known and are available from the prior art. A definition of ZSM-12 is given in the "Database of zeolite structures" published in 2007/2008 by the "Structure Commission of the International Zeolite Association".

Advantageously, the zeolite content is in the range 1% to 20% by weight with respect to the mass of the support, the support corresponding to a mixture of zeolite and matrix.

The catalyst of the invention is preferably composed of:
- 1% to 20% by weight, limits included, preferably 1% to 10% by weight, limits included, of at least one zeolite with structure type MTW comprising silicon and at least one element T selected from the group formed by aluminium, iron, gallium and boron, with a Si/T atomic ratio in the range 20 to 200, limits included, preferably in the range 20 to 100, limits included. Preferably, said element T is selected from the group constituted by aluminium and boron; more preferably, the element T is aluminium,
- 0.01% to 2% by weight, limits included, preferably 0.05% to 1% by weight, limits included, of at least one metal from group VIII of the periodic classification of the elements, said metal from group VIII being deposited on the zeolite or on the binder,
- the complement to 100% by weight of at least one matrix.

The overall Si/Al atomic ratio, determined by X ray fluorescence or atomic absorption, takes into account both the aluminium atoms present in the zeolitic framework and the aluminium atoms which may be present outside said zeolitic framework, also termed extra-framework aluminium. Advantageously, the zeolite with structure type MTW used has a Si/Al ratio in the range 20 to 200, limits included, preferably in the range 20 to 100, limits included.

Catalyst Preparation Process

The present invention also concerns a process for the preparation of the catalyst in accordance with the invention.

The catalyst of the invention is prepared using a process comprising the following steps:
i) using at least one zeolite with structure type MTW,
ii) preparing a support by shaping said zeolite with a matrix,
iii) depositing at least one metal from group VIII of the periodic classification of the elements onto said support or onto said zeolite, the order of carrying out said steps ii) and iii) being unimportant following said step i),
iv) bringing the catalyst obtained in step ii) or step iii), depending on the order in which they are carried out, into contact with steam at a partial pressure in the range 0.01 to 0.07 MPa, at a temperature in the range 300° C. to 400° C., for at least 0.5 hour, in a manner such that the mesopore volume of the catalyst is increased by at least 10% compared with the initial mesopore volume of the catalyst, which is generally in the range 0.55 to 0.75 mL/g.

Preferably, the steam used is diluted in a neutral gas, dioxygen or in air.

Advantageously, the zeolite with structure type MTW used in step i) has a Si/Al ratio in the range 20 to 200, limits included, preferably in the range 20 to 100, limits included.

Advantageously, in step ii) the zeolite with structure type MTW is shaped with a matrix with a zeolite content in the range 1% to 20% by weight, preferably in the range 1% to 10% by weight with respect to the mass of the support.

Advantageously, the steam treatment of step iv) is carried out with a partial pressure of steam in the range 0.04 to 0.06 MPa, preferably diluted in air.

Advantageously, the steam treatment of step iv) is carried out at a temperature in the range 300° C. to 380° C. for 0.5 hour to 24 hours, preferably in the range 1 hour to 12 hours.

Advantageously, the flow rate of the gas formed by steam is in the range 0.2 to 10 L/h/g (litres per hour per gram) of zeolitic support.

Ionic Exchange

Said zeolite with structure type MTW which comprises the catalyst of the invention is at least partially in the acid form, i.e. in the hydrogen form (H); the competing cation C is selected from the group constituted by alkali or alkaline-earth cations, preferably from the group constituted by the cations $Na^+$ and $K^+$; preferably, the competing cation C is the cation $Na^+$.

An ionic exchange preceded by calcining may be carried out after step i) in the presence of ammonium nitrate or ammonium acetate at a concentration of 0.005 to 15 N, preferably 0.1 to 10 N, at a temperature in the range 15° C. to 100° C., for a period of 1 to 10 hours in a batch or continuous reactor. In general after the exchange step, the zeolite obtained is dried, for example oven dried, at a temperature in the range from ambient temperature to 250° C., before being calcined at a temperature in the range 300° C. to 600° C. in air. It is possible to carry out successive exchanges. The exchange or exchanges may be carried out on the zeolite of the support after step ii).

Preparation of the Support

The shaping step (step ii)) is generally such that the catalyst is preferably in the form of extrudates or beads depending on their use. In a variation of the catalyst preparation, shaping is carried out before calcining and ion exchange.

In order to carry out said step ii) for preparation of the support, any alumina which is known to the skilled person with any specific surface area and pore volume is used; preferably, the matrix is selected from clays, magnesia, aluminas, silicas, titanium oxide, boron oxide, zirconia, aluminium phosphates, titanium phosphates, zirconium phosphates and silica-aluminas. Charcoal may also be used. Preferably, the matrix is an alumina.

The quantity of zeolite in the support is in the range 1% to 20% by weight, preferably in the range 1% to 10% by weight.

Drying and Calcining of the Support

The preparation of the support in accordance with said step ii) is advantageously followed by drying then by calcining. Drying is preferably carried out at a temperature in the range 100° C. to 150° C. for a period in the range 5 to 20 hours in an oven. Calcining is preferably carried out at a temperature in the range 250° C. to 600° C. for a period in the range 1 to 8 hours.

Deposition of Metal

In accordance with the invention, step iii) for preparing the catalyst comprising a zeolite with structure type MTW, preferably a ZSM-12 zeolite, consists of depositing at least one metal from group VIII of the periodic classification of the elements and optionally at least one metal selected from metals from groups IIIA, IVA and VIIB.

Said metal from group VIII present in the catalyst of the invention is selected from iron, cobalt, nickel, ruthenium, rhodium, palladium, osmium, iridium and platinum, preferably from the noble metals and more preferably from palladium and platinum. Even more preferably, said metal from group VIII is platinum. Depending on the method used to deposit said metal from group VIII, as indicated below in the description, said metal from group VIII, preferably platinum, may be deposited primarily on the zeolite or on the matrix.

The metal selected from metals from groups IIIA, IVA and VIIB and optionally present in the catalyst of the invention is selected from gallium, indium, tin and rhenium, preferably from indium, tin and rhenium.

The catalyst of the invention may be prepared using any method known to the skilled person. Preferably, following calcining carried out at the end of step ii) on the support, at least one metal VIII is introduced onto the support, namely mainly on the matrix, or mainly on the zeolite or indeed on the zeolite-matrix ensemble. Said metal is advantageously deposited onto the support using the dry impregnation technique or the excess impregnation technique. When a plurality of metals is introduced, these may be introduced either all in the same manner or using different techniques.

Any precursor of the metals from group VIII is suitable for depositing one or more metal(s) from group VIII onto the support. In particular, for any noble metal from group VIII, it is possible to use ammonia compounds or compounds such as, for example, ammonium chloroplatinate, platinum dicarbonyl dichloride, hexahydroxyplatinic acid, palladium chloride or palladium nitrate. The platinum is generally introduced in the form of hexachloroplatinic acid. The noble metal from group VIII is preferably introduced by impregnation using an aqueous or organic solution of one of the metallic compounds cited above. Examples of organic solvents which may be used and which may be cited are paraffinic, naphthenic or aromatic hydrocarbons containing 6 to 12 carbon atoms per molecule, for example, and halogenated organic compounds containing 1 to 12 carbon atoms per molecule, for example. Examples which may be cited are n-heptane, methylcyclohexane, toluene and chloroform. It is also possible to use mixtures of solvents.

Controlling certain parameters employed during deposition, in particular the nature of the precursor of the metal(s) from group VIII used, means that deposition of said metal(s) can be orientated towards mainly the matrix or mainly the zeolite.

Thus, in order to introduce the metal(s) from group VIII, preferably platinum and/or palladium, primarily onto the matrix, it is possible to use an anionic exchange with hexachloroplatinic acid and/or hexachloropalladic acid, in the presence of a competing agent, for example hydrochloric acid, deposition generally being followed by calcining, for example at a temperature in the range 350° C. to 550° C. and for a period in the range 1 to 4 hours. With precursors of this type, the metal(s) from group VIII is (are) deposited mainly on the matrix and said metal(s) have good dispersion and good macroscopic distribution through the catalyst grain.

It is also possible to envisage depositing the metal(s) from group VIII, preferably platinum and/or palladium, by cationic exchange such that said metal(s) is (are) deposited mainly on the zeolite. Thus, in the case of platinum, the precursor may, for example, be selected from: ammonia compounds such as platinum (II) tetrammine salts with formula $Pt(NH_3)_4X_2$, platinum (IV) hexammine salts with formula $Pt(NH_3)_6X_4$; platinum (IV) halogenopentammine salts with formula $(PtX(NH_3)_5)X_3$; platinum N-tetrahalogenodiamine salts with formula $PtX_4(NH_3)_2$; and halogenated compounds with formula $H(Pt(acac)_2X)$;

X being a halogen selected from the group formed by chlorine, fluorine, bromine and iodine, X preferably being chlorine, and "acac" representing the acetylacetonate group (with empirical formula $C_5H_7O_2$), a derivative of acetylacetone. With precursors of this type, the metal(s) from group VIII is (are) deposited mainly on the zeolite and said metal(s) have good dispersion and good macroscopic distribution through the catalyst grain.

Dry impregnation of the metal from group VIII onto the support results in said metal being deposited both on the matrix and on the zeolite.

In the case in which the catalyst of the invention also contains at least one metal selected from metals from groups IIIA, IVA and VIIB, any of the techniques for depositing a metal of this type which is known to the skilled person and any precursors of metals of this type may be suitable.

It is possible to add the metal(s) from group VIII and that (those) from groups IIIA, IVA and VIIB, either separately or simultaneously in at least one unitary step. When at least one metal from groups IIIA, IVA and VIIB is added separately, it is preferable for it to be added after the metal from group VIII.

The additional metal selected from metals from groups IIIA, IVA and VIIB may be introduced via compounds such as chlorides, bromides and nitrates of metals from groups IIIA, IVA and VIIB, for example. As an example in the case of indium, the nitrate or chloride may advantageously be used, and in the case of rhenium, perrhenic acid is advantageously used. In the case of tin, the tin chlorides $SnCl_2$ and $SnCl_4$ are preferred. The additional metal selected from metals from groups IIIA, IVA and VIIB may also be introduced in the form of at least one organic compound selected from the group constituted by complexes of said metal, in particular polyketone complexes of the metal, and metal hydrocarbyls such as metal alkyls, cycloalkyls, aryls, alkylaryls and arylalkyls. In this latter case, the metal is advantageously introduced with the aid of a solution of an organometallic compound of said metal in an organic solvent. It is also possible to use organohalogenated metal compounds. Examples of organic compounds of metals which may in particular be cited are tetrabutyltin in the case of tin, and triphenylindium in the case of indium.

If the additional metal selected from metals from groups IIIA, IVA and VIIB is introduced before the metal from group VIII, the compound of the IIIA, IVA and VIIB group metal used is generally selected from the group constituted by the metal halide, nitrate, acetate, tartrate, carbonate and oxalate. The introduction is then advantageously carried out in aqueous solution. However, it may also be introduced with the aid of a solution of an organometallic compound of the metal, for example tetrabutyltin. In this case, before proceeding to introducing at least one metal from group VIII, calcining is carried out in air.

In addition, intermediate treatments such as calcining and/or reduction, for example, may be applied between the successive depositions of the various metals.

Advantageously, deposition of the metal(s) is followed by calcining, normally at a temperature in the range 250° C. to 600° C., for a period in the range 0.5 to 10 hours, preferably preceded by drying, for example oven drying, at a temperature from ambient temperature to 250° C., preferably in the range 40° C. to 200° C. Said drying step is preferably carried out during the temperature rise necessary for carrying out said calcining.

The metal(s) from group VIII, preferably platinum, deposited on the zeolite and/or on the matrix, represent 0.01% to 2% by weight, preferably 0.05% to 1% by weight with respect to the catalyst weight. The matrix constitutes the complement to 100%.

When said catalyst contains at least one metal selected from metals from groups IIIA, IVA and VIIB, the quantity thereof may be up to 2% by weight with respect to the catalyst weight. It is then advantageously 0.01% to 2%, preferably 0.05% to 1% by weight. When said catalyst contains sulphur, the quantity thereof may be such that the ratio of the number of sulphur atoms to the number of metal from group VIII atoms deposited is up to 2:1. It is thus advantageously 0.5:1 to 2:1.

Steam Treatment

In accordance with the invention, after step ii) or after step iii), said catalyst undergoes a steam treatment such that its mesopore volume is increased by at least 10%, preferably by at least 10.5% compared with its initial mesopore volume, said initial mesopore volume generally being in the range 0.55 to 0.75 mL/g. The increase in the mesoporosity may be more than 15% by weight. To this end, the treatment in the presence of steam which the catalyst undergoes after step ii) or after step iii) is carried out under controlled conditions, namely: at a temperature in the range 300° C. to 400° C., preferably in the range 300° C. to 380° C., still more preferably in the range 330° C. to 370° C. The duration of said treatment is at least 0.5 hours, preferably in the range 0.5 hour to 24 hours, and more preferably in the range 1 hour to 12 hours. The partial pressure of steam during the treatment is advantageously in the range 0.01 to 0.07 MPa, preferably 0.04 to 0.06 MPa. The steam is generally diluted in a neutral gas, dioxygen or air, preferably in air.

The flow rate of the gas formed by steam is advantageously in the range 0.2 L/h/g to 10 L/h/g of zeolitic support.

It is possible to carry out prior reduction of the catalyst ex situ or in situ, in a current of hydrogen, for example at a temperature of 450° C. to 600° C., for a period of 0.5 to 4 hours, before carrying out the isomerization process.

In the case in which the catalyst does not contain sulphur, a reduction of the metal in hydrogen is advantageously carried out in situ before injecting the feed.

In the case in which the catalyst used in the invention contains sulphur, the sulphur is introduced onto the shaped and calcined catalyst containing the metal or metals cited above, either in situ before the catalytic reaction, or ex situ. Optional sulphurization is carried out after the reduction. In the case of an in situ sulphurization, if the catalyst has not already been reduced, reduction is carried out before sulphurization. In the case of an ex situ sulphurization, reduction is carried out then sulphurization. The sulphurization is carried out in the presence of hydrogen using any sulphurization agent which is known to the skilled person, such as dimethyl sulphide or hydrogen sulphide, for example. As an example, the catalyst is treated with a feed containing dimethyl sulphide in the presence of hydrogen, with a concentration such that the sulphur/metal atomic ratio is 1.5. The catalyst is then held for approximately 3 hours at approximately 400° C. in a flow of hydrogen before injecting the feed.

The isomerization process of the invention consists of bringing an aromatic cut containing at least one aromatic compound containing eight carbon atoms per molecule into contact with at least said catalyst containing at least said zeolite with structure type MTW, preferably said ZSM-12 zeolite, said catalyst having been prepared in accordance with the procedure of each of said steps i), ii), iii) and iv) described above in the present description.

Isomerization Process

The present invention also concerns a process for the isomerization of a feed in the presence of the catalyst of the invention.

The feed of the invention is an aromatic cut containing at least one aromatic compound containing eight carbon atoms per molecule and advantageously comprises either a mixture of xylenes alone or ethylbenzene alone, or a mixture of xylene(s) and ethylbenzene.

The isomerization process of the invention comprises bringing said cut into contact with the catalyst of the invention.

The isomerization process of the invention is advantageously carried out using the following operating conditions:
- a temperature of 300° C. to 500° C., preferably 320° C. to 450° C. and more preferably 340° C. to 430° C.;
- a partial pressure of hydrogen of 0.3 to 1.5 MPa, preferably 0.4 to 1.2 MPa and still more preferably 0.7 to 1.2 MPa;
- a total pressure of 0.45 to 1.9 MPa, preferably 0.6 to 1.5 MPa; and
- a supply space velocity, expressed as kilograms of feed introduced per kilogram of catalyst per hour, of 0.25 to 30 $h^{-1}$, preferably 1 to 10 $h^{-1}$, and more preferably 2 to 6 $h^{-1}$.

The following examples illustrate the invention without in any way limiting its scope.

EXAMPLES

Example 1 (In Accordance with the Invention): Preparation of Catalyst A Treated with Steam at 350° C., Containing ZSM-12 Zeolite and 0.3% by Weight of Platinum The starting material used was an as-synthesized ZSM-12 zeolite comprising the organic template, silicon and aluminium, having a Si/Al atomic ratio of 60. This ZSM-12 zeolite underwent calcining at 550° C. in a stream of air for 6 hours.

The calcined ZSM-12 zeolite was then shaped by extrusion with an alumina gel in order to obtain, after drying and calcining in dry air, a support constituted by extrudates 1.4 mm in diameter which contained approximately 4% by weight of ZSM-12 zeolite and approximately 96% by weight of alumina. The mesopore volume of the support was determined from the nitrogen adsorption isotherm and was 0.73 mL/g.

The support obtained then underwent anionic exchange with hexachloroplatinic acid in the presence of a competing agent (hydrochloric acid) so as to deposit 0.3% by weight of platinum with respect to the catalyst. The moist solid was then dried at 120° C. for 12 hours and calcined in air at a temperature of 500° C. for one hour.

The solid was then treated with steam with a partial pressure of 0.05 MPa in 2 L/h/g of air at 350° C. for 10 hours. After treatment, the mesopore volume of the catalyst was determined from the nitrogen adsorption isotherm and was 0.81 mL/g.

The catalyst obtained contained 4% by weight of ZSM-12 zeolite partially in the hydrogen (H) form, 95.7% by weight of alumina and 0.3% by weight of platinum. The platinum dispersion was approximately 80%, measured by oxygen chemisorption.

Example 2 (Not in Accordance with the Invention): Preparation of Catalyst B Without Treatment with Steam, Containing ZSM-12 Zeolite and 0.3% by Weight of Platinum The starting material used was an as-synthesized ZSM-12 zeolite comprising the organic template, silicon and aluminium, having a Si/Al atomic ratio of 60. This ZSM-12 zeolite underwent calcining at 550° C. in a stream of air for 6 hours.

The calcined ZSM-12 zeolite was then shaped by extrusion with an alumina gel in order to obtain, after drying and calcining in dry air, a support constituted by extrudates 1.4 mm in diameter which contained approximately 4% by weight of ZSM-12 zeolite and approximately 96% by weight of alumina. The mesopore volume of the support was determined from the nitrogen adsorption isotherm and was 0.73 mL/g.

The support obtained then underwent anionic exchange with hexachloroplatinic acid in the presence of a competing agent (hydrochloric acid) so as to deposit 0.3% by weight of platinum with respect to the catalyst. The moist solid was then dried at 120° C. for 12 hours and calcined in air at a temperature of 500° C. for one hour.

The catalyst obtained contained 4% by weight of ZSM-12 zeolite partially in the hydrogen (H) form, 95.7% by weight of alumina and 0.3% by weight of platinum. The platinum dispersion was approximately 80%, measured by oxygen chemisorption.

Example 3 (Not in Accordance with the Invention): Preparation of Catalyst C Treated with Steam at 550° C., Containing ZSM-12 Zeolite and 0.3% by Weight of Platinum The starting material used was an as-synthesized ZSM-12 zeolite comprising the organic template, silicon and aluminium, having a Si/Al atomic ratio of 60. This ZSM-12 zeolite underwent calcining at 550° C. in a stream of air for 6 hours.

The calcined ZSM-12 zeolite was then shaped by extrusion with an alumina gel in order to obtain, after drying and calcining in dry air, a support constituted by extrudates 1.4 mm in diameter which contained approximately 4% by weight of ZSM-12 zeolite and approximately 96% by weight of alumina. The mesopore volume of the support was determined from the nitrogen adsorption isotherm and was 0.73 mL/g.

The support obtained then underwent anionic exchange with hexachloroplatinic acid in the presence of a competing agent (hydrochloric acid) so as to deposit 0.3% by weight of platinum with respect to the catalyst. The moist solid was then dried at 120° C. for 12 hours and calcined in air at a temperature of 500° C. for one hour.

The solid was then treated with steam with a partial pressure of 0.09 MPa in 2 L/h/g of air at 550° C. for 10 hours. After treatment, the mesopore volume of the catalyst was determined from the nitrogen adsorption isotherm and was 0.75 mL/g.

The catalyst obtained contained 4% by weight of ZSM-12 zeolite partially in the hydrogen (H) form, 95.7% by weight of alumina and 0.3% by weight of platinum. The platinum dispersion was approximately 80%, measured by oxygen chemisorption.

Example 4: Evaluation of Catalytic Properties of Catalysts A, B and C for the Isomerization of an Aromatic C8 Cut in Accordance with the Process of the Invention The performances of the catalysts A, B and C were evaluated for the isomerization of a C8 aromatic cut containing principally meta-xylene, ortho-xylene and ethylbenzene. The characteristics of the feed were as follows:

| Feed | % by weight |
|---|---|
| Ethylbenzene | 19 |
| Ortho-xylene | 14.4 |
| Meta-xylene | 60 |

The catalysts were held at 480° C. for 3 hours in a flow of pure hydrogen, then the feed was injected.

Catalysts A, B and C were brought into contact with the feed; the operating conditions were as follows:
Temperature=385° C.,
Total pressure=1 MPa,
Partial pressure of hydrogen (ppH$_2$)=0.88 MPa,
Space velocity (HSV)=8 h$^{-1}$ The catalysts were compared in terms of activity (by the approach to equilibrium for para-xylene and by the ethylbenzene conversion).

In order to calculate the approach to equilibrium for para-xylene (AEQ pX), the concentration of para-xylene (% pX) is expressed with respect to the three xylene isomers.

The approach to equilibrium for para-xylene (AEQ pX) is defined as follows:

$$\text{AEQ } pX\ (\%) = 100 \times (\%\ pX_{\text{effluent}} - \%\ pX_{\text{feed}})/(\%\ pX_{\text{equilibrium}} - \%\ pX_{\text{feed}})$$

where
% pX$_{\text{effluent}}$=concentration of para-xylenes in the effluent at the end of the reaction,
% pX$_{\text{feed}}$=concentration of para-xylenes initially present in the feed,
% pX equilibrium=concentration of para-xylenes at equilibrium.

The ethylbenzene conversion, Cv EB (%), is defined as follows:

$$Cv\ EB\ (\%) = 100 \times (\%\ EB_{\text{feed}} - \%\ EB_{\text{effluent}})/\%\ EB_{\text{feed}}$$

where
% EB$_{\text{feed}}$=concentration of ethylbenzene initially present in the feed,
% EB$_{\text{effluent}}$=concentration of ethylbenzene present in the effluent at the end of the reaction.

The results obtained under iso-operating conditions are presented in Table 1.

TABLE 1

Activity of catalysts A, B et C after 4000 minutes of reaction

| Activity (%) | Catalyst A | Catalyst B | Catalyst C |
|---|---|---|---|
| AEQ pX | 91.1 | 82.0 | 77.4 |
| Cv EB | 31.0 | 17.5 | 14.7 |

Catalyst A treated with steam at 350° C. with a partial pressure of water of 0.05 MPa exhibited a substantial increase in the ethylbenzene conversion as well as an activity, as the approach to thermodynamic equilibrium for para-xylene, which was substantially increased compared with the catalysts which had not undergone the steam treatment (catalyst B) and which had undergone a steam treatment at a temperature above 400° C. and at a partial pressure of water of more than 0.07 MPa (catalyst C).

The invention claimed is:
1. A process for the preparation of a catalyst comprising at least one zeolite with structure type MTW, a matrix, and at least one metal from group VIII of the periodic classification of the elements, comprising at least the following steps:

i) providing at least one zeolite with structure type MTW,
ii) preparing a support by shaping said zeolite with a matrix,
iii) depositing at least one metal from group VIII of the periodic classification of the elements onto said support or onto said zeolite, wherein the depositing can be before or after the preparing of the support in step ii),
iv) bringing the catalyst obtained in step ii) or step iii), depending on the order in which they are carried out, into contact with steam at a partial pressure in the range 0.01 to 0.07 MPa, at a temperature in the range 300° C. to 400° C., for at least 0.5 hour, in a manner such that the mesopore volume of the catalyst is increased by at least 10% compared with the mesopore volume of the catalyst before the contact with steam.

2. The process according to claim 1, wherein step ii) is conducted before step iii) and, before step iii), step ii) is followed by drying carried out at a temperature in the range 100° C. to 150° C. for a period in the range 5 to 20 hours in an oven, then by calcining carried out at a temperature in the range 250° C. to 600° C. for a period in the range 1 to 8 hours.

3. The process according to claim 1, wherein step iii) for depositing the metal(s) is followed by calcining at a temperature in the range 250° C. to 600° C., for a period in the range 0.5 to 10 hours, preceded by drying at a temperature from ambient temperature to 250° C., provided that, if step iii) is conducted before step ii), then the calcining is conducted after step iii) and before step ii).

4. The process according to claim 1, wherein the catalyst is reduced ex situ or in situ before it is used, in a stream of hydrogen at a temperature of 450° C. to 600° C., for a period of 0.5 to 4 hours.

5. The process according to claim 1, wherein the steam is at a partial pressure in the range 0.04 to 0.06 MPa.

6. The process according to claim 1, wherein the steam used is diluted in a neutral gas, in dioxygen or in air.

7. The process according to claim 1, wherein the temperature at which the catalyst is brought into contact with steam is in the range 300° C. to 380° C.

8. The process according to claim 1, wherein the overall atomic ratio Si/Al of the zeolite with structure type MTW is in the range 20 to 200, limits included.

9. The process according to claim 1, wherein the zeolite content is in the range 1% to 20% by weight with respect to the mass of the support, the support representing the mixture of zeolite and matrix.

10. The process according to claim 1, wherein the matrix is selected from clays, magnesia, aluminas, silicas, titanium oxide, boron oxide, zirconia, aluminium phosphates, titanium phosphates, zirconium phosphates, silica-aluminas and charcoal or a mixture of at least two of these compositions.

11. The process according to claim 1, wherein the matrix is an alumina.

12. The process according to claim 1, wherein the zeolite with structure type MTW is selected from: ZSM-12, CZH-5, NU-13, TPZ-12, Theta-3 and VS-12.

13. The process according to claim 1, further comprising carrying out isomerization of an aromatic cut containing at least one aromatic compound containing 8 carbon atoms per molecule, by bringing said cut into contact with the catalyst prepared by the process of claim 1.

14. The process according to claim 13, wherein the isomerization is carried out at a temperature of 300° C. to 500° C., a partial pressure of hydrogen of 0.3 to 1.5 MPa, a total pressure of 0.45 to 1.9 MPa and a feed space velocity, expressed as kilograms of feed introduced per kilogram of catalyst per hour, of 0.25 to 30 $h^{-1}$.

15. The process according to claim 13, wherein the aromatic cut comprises a mixture of xylenes alone, or ethylbenzene alone, or a mixture of xylene(s) and ethylbenzene.

16. The process according to claim 1, wherein the mesopore volume of the catalyst prepared by the process is at least 0.605 mL/g.

17. The process according to claim 1, wherein the overall atomic ratio Si/Al of the zeolite with structure type MTW is in the range 20 to 100, limits included.

18. The process according to claim 1, wherein the zeolite content is in the range 1% to 10% by weight with respect to the mass of the support, the support representing the mixture of zeolite and matrix.

19. The process according to claim 1, wherein the zeolite with structure type MTW is ZSM-12 zeolite.

20. The process according to claim 1, wherein the mesopore volume of the catalyst before the contact with steam is in the range 0.55 to 0.75 mL/g.

* * * * *